(12) United States Patent
Gerber et al.

(10) Patent No.: US 6,242,417 B1
(45) Date of Patent: Jun. 5, 2001

(54) STABILIZED COMPOSITIONS CONTAINING HEMOGLOBIN

(75) Inventors: Michael J. Gerber, Denver; Douglas L. Looker; Bruce A. Kerwin, both of Lafayette, all of CO (US)

(73) Assignee: Somatogen, Inc., Boulder, CO (US)

(*) Notice: Subject to any disclaimer, the term of this patent is extended or adjusted under 35 U.S.C. 154(b) by 0 days.

(21) Appl. No.: 08/417,644

(22) Filed: Apr. 5, 1995

Related U.S. Application Data

(63) Continuation-in-part of application No. 08/399,899, filed on Mar. 7, 1995, now abandoned, which is a continuation-in-part of application No. 08/208,740, filed on Mar. 8, 1994.

(51) Int. Cl.[7] ............... A61K 38/16; A01N 1/02; G01N 33/72; G01N 31/00
(52) U.S. Cl. ............ 514/6; 435/2; 436/66; 436/63; 436/16; 436/15; 436/74
(58) Field of Search ............ 514/6; 435/2; 436/66, 436/63, 16, 15, 74

(56) References Cited

U.S. PATENT DOCUMENTS

| | | | |
|---|---|---|---|
| 3,847,545 | * 11/1974 | Shanbrom et al. | 436/66 |
| 3,997,470 | * 12/1976 | Monte et al. | 436/74 |
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,061,736 | 12/1977 | Morris et al. | 424/177 |
| 4,301,144 | 11/1981 | Iwashita et al. | 424/78 |
| 4,321,259 | 3/1982 | Nicolau et al. | 424/101 |
| 4,336,248 | 6/1982 | Bonhard | 424/101 |
| 4,377,512 | 3/1983 | Ajisaka et al. | 260/112 B |
| 4,401,652 | 8/1983 | Simmonds | 424/101 |
| 4,412,989 | 11/1983 | Iwashita et al. | 424/177 |
| 4,439,357 | 3/1984 | Bonhard et al. | 260/112 B |

(List continued on next page.)

FOREIGN PATENT DOCUMENTS

| | | |
|---|---|---|
| 0132178 | 1/1985 | (EP). |
| 0277289 | 8/1988 | (EP). |
| 0206448 | 11/1990 | (EP). |
| 0231236 | 10/1991 | (EP). |
| 0459788 | 12/1991 | (EP). |
| 0277289 | 4/1992 | (EP). |
| 0361719 | 1/1994 | (EP). |
| 8806161 | 8/1988 | (WO). |
| 8904168 | 5/1989 | (WO). |
| 8912456 | 12/1989 | (WO). |
| 9013645 | 11/1990 | (WO). |
| 9105795 | 5/1991 | (WO). |
| 9109615 | 7/1991 | (WO). |
| 9110439 | 7/1991 | (WO). |
| 9202239 | 2/1992 | (WO). |
| 9202242 | 2/1992 | (WO). |
| 9203153 | 3/1992 | (WO). |
| 9209630 | 6/1992 | (WO). |
| 9211283 | 7/1992 | (WO). |
| 9211355 | 7/1992 | (WO). |
| 9221702 | 12/1992 | (WO). |
| 9222646 | 12/1992 | (WO). |
| 9309143 | 5/1993 | (WO). |
| 9318132 | 9/1993 | (WO). |
| 9318136 | 9/1993 | (WO). |
| 9318137 | 9/1993 | (WO). |
| 9401452 | 1/1994 | (WO). |

OTHER PUBLICATIONS

Theodorsen, L.; Scand J. Clin Lab Invest 1990; 50: 643–648.*

(List continued on next page.)

*Primary Examiner*—Louise Leary
(74) *Attorney, Agent, or Firm*—Marianne F. Novelli; Theresa A. Brown

(57) ABSTRACT

The present invention relates to a hemoglobin compositions stabilized against the formation of aggregates. The present invention further relates to methods of making such hemoglobin compositions.

18 Claims, 2 Drawing Sheets

U.S. PATENT DOCUMENTS

| | | | |
|---|---|---|---|
| 4,473,494 | 9/1984 | Tye | 260/112 B |
| 4,473,496 | 9/1984 | Scannon | 260/112 B |
| 4,473,563 | 9/1984 | Nicolau et al. | 424/224 |
| 4,526,715 | 7/1985 | Kothe | 260/112 B |
| 4,529,719 | 7/1985 | Tye | 514/6 |
| 4,584,130 | 4/1986 | Bucci et al. | 260/112 B |
| 4,598,064 | 7/1986 | Walder | 514/6 |
| 4,600,531 | 7/1986 | Walder | 530/385 |
| 4,626,511 * | 12/1986 | Artiss et al. | 436/15 |
| 4,645,830 | 2/1987 | Yasushi et al. | 530/351 |
| 4,650,786 | 3/1987 | Wong | 514/6 |
| 4,670,417 | 6/1987 | Iwasaki et al. | 514/6 |
| 4,703,008 | 10/1987 | Lin | 435/240.2 |
| 4,710,488 | 12/1987 | Wong | 514/6 |
| 4,777,244 | 10/1988 | Bonhard et al. | 530/385 |
| 4,810,643 | 3/1989 | Souza | 435/68 |
| 4,826,811 | 5/1989 | Sehgal et al. | 514/6 |
| 4,857,636 | 8/1989 | Hsia | 530/385 |
| 4,861,867 | 8/1989 | Estep | 530/385 |
| 4,868,119 | 9/1989 | Clark et al. | 435/240.2 |
| 4,876,188 * | 10/1989 | Smith et al. | 436/66 |
| 4,880,749 * | 11/1989 | Burdick et al. | 436/66 |
| 4,920,194 | 4/1990 | Feller et al. | 530/385 |
| 4,965,251 | 10/1990 | Stamatoyannopoulos | 514/8 |
| 5,004,681 | 4/1991 | Boyse et al. | 435/2 |
| 5,028,588 | 7/1991 | Hoffman et al. | 514/6 |
| 5,032,396 | 7/1991 | Williams | 424/85.2 |
| 5,032,507 | 7/1991 | Yu et al. | 435/29 |
| 5,032,676 | 7/1991 | Deeley et al. | 530/351 |
| 5,061,620 | 10/1991 | Tsukamoto et al. | 435/7.21 |
| 5,084,558 | 1/1992 | Rausch | 530/385 |
| 5,096,885 | 3/1992 | Pearlman et al. | 514/12 |
| 5,104,653 | 4/1992 | Michalevicz | 424/85.6 |
| 5,188,828 | 2/1993 | Goldberg et al. | 424/85.2 |
| 5,194,590 | 3/1993 | Sehgal et al. | 530/385 |
| 5,198,417 | 3/1993 | Donahue | 514/2 |
| 5,199,942 | 4/1993 | Gillis | 604/4 |
| 5,234,903 * | 8/1993 | Nho et al. | 514/6 |
| 5,238,963 * | 8/1993 | Cerami et al. | 514/6 |
| 5,242,832 * | 9/1993 | Sakata | 436/63 |
| 5,250,665 | 10/1993 | Kluger et al. | 530/385 |
| 5,264,208 | 11/1993 | Hughes | 424/85.1 |
| 5,296,465 | 3/1994 | Rausch | 514/6 |

OTHER PUBLICATIONS

Looker, D. et al/Expression of Recombinant Human Hemoglobin in *Escherichia Coli*/Methods in Enzymology (1994) 231: 364–374, Month not available.

Kaye, F.J. et al/The Effect of Hemin In Vitro and In Vivo on Human Erythroid Progenitor Cells/International J. of Cell Cloning/(1986)4: 432–446, Month not available.

Fratantoni, J.C./Points to Consider in the Safety Evaluation of Hemoglobin–Based Oxygen Carriers/Transfusion/(1991) 31(4): 369–371, Month not available.

Coulombel, L. et al/Hemoglobin Content of Individual Erythroblasts In Hematopoietic Dyplasia: Marked Heterogeneity at Late Stages of Maturation/Exp. Hematol./(1984) 12:587–593, Month not available.

Grutzmacher, P. et al/Effect of Recombinant Human Erythropoietin on Iron Balance in Maintenance Hemodialysis: Theoretical Considerations, Clinical Experience and Consequences/Clinical Nephrology/ (1992) 38 Suppl. 1: 592–597, Month not available.

Eschbach, J.W. et al/Correction of the Anemia of End–Stage Renal Disease with Recombinant Human Erythropoietin/ New England J. of Medicine/(1987) 316(2): 73–78, Month not available.

Hawkins, W.B. & Johnson, A.C./Bile Pigment and Hemoglobin Interrelation in Anemic Dogs/Am. J. Physiol./(1939) 126: 326–336, Month not available.

Ferrari, R./Ricerche Sulla Formazione Della Emoglobina Nella Rana Salata/Archivio DI Scienze Biologiche/Ed. Cappelli/(1932) 17: 25–40, Month not available.

Amberson. W.R./Blood Substitutes/Biol. Res./(1937) 12: 48–86, Month not available.

Furuka WA. K./Experimentelle Untersuchungen Zur Chirurgischen Anamiebehandlung Durch Autotransfusion Von Blut/Klin. Wochenschrift/(1922) 1: 723–725, Month not available.

Monette, F.C. & Sigounas, G./Hemin Acts Synergistically with Interleukin–3 to Promote the Growth of Multipotent Stem Cells (CFU–GEMM) in "Serum–Free" Cultures of Normal Murine Bone Marrow/Exp. Hematol/(1988) 16: 727–729, Month not available.

Monette. F.C./The Role of Interleukin–3 and Heme in the Induction of Erythropoiesis/Ann. NY Acad. SCL/(1989) 554: 49–58, Month not available.

Monette, F.C. et al/Specificity of Hemin Action In Vivo at Early Stages of Hematopoietic Cell Differentiation/Exp. Hematol./(1984) 12: 782–787, Month not available.

Holden, S.A. et al/Further Characterization of the Hemin–Induced Enhancement of Primitive Erythroid Progenitor Cell Growth In Vitro/Exp. Hematol./(1983) 11(10): 953–960.

Porter, P.N. et al/Enhancement of Erythroid Colony Growth in Culture by Hemin/Exp. Hemat./(1979) 7(1): 11–16, Month not available.

Dabney, B.J. & Beaudet. Al./Increase in Globin Chains and Globin mRNA in Erythroleukemia Cells in Response to Hemin/Arch. Biochem. & Biophys./(1977) 179: 106–112, Month not available.

Ross, J. & Sautner, D./Induction of Globin mRNA Accumulation by Hemin in Cultured Erythroleukemic Cells/Cell/ (1976) 8: 513–520, Month not available.

Feola, M. et al/Nephrotoxicity of Hemoglobin Solutions/ Biomat.,Art. Cell.Art.Org./(1990) 18(2): 233–249, Month not available.

Feola, M. et al/Clinical Trial a of Hemoglobin Based Blood Substitute in Patients with Sickel Cell Anemia/Surgery. Gyn. & Ob./(1992) 174: 379–386, Month not available.

Chertkov, J.L. et al/Hematopoietic Effects of Benzene Inhalation Assessed by Murine Long–Term Bone Marrow Culture/J. of Lab. & Clin. Med./(1992) 119(4): 412–419, Month not available.

Abraham, N.G. et al/Comparison of Hemin Enhancement of Burst–Forming Units–Erythroid Clonal Efficiency by Progenitor Cells from Normal and HIV–Infected Patients/Acta Haem./(1991) 86: 189–193, Month not available.

Cipolleschi, M.G. et al/The Role of Hypoxia in the Maintenance of Hematopoietic Stem Cells/Blood/(1993) 82(7): 2031–2037, Month not available.

Van Zant, G./Studies of Hematopoietic Stem Cells Spared by 5–Fluorouracil/J. Exp. Med./(1984) 159: 679–690, Month not available.

Abraham, N.G. et al/Microenvironmental Toxicity of Azidothymidine: Partial Sparing with Hemin/Blood/(1989) 74(1): 139–144, Month not available.

Reincke, U. et al/Adherent Stem Cells: Frequency in Mouse Marrow and Terminal Clone Sizes in Long–Term Culture/ Exp. Hematol./(1985) 13: 545–553, Month not available.

Quesenberry. P.J./The Concept of the Hemopoietic Stem Cell–Hemopoietic Stem Cells, Progenitor Cells, and Growth Factors/Hematology/(1990) 129–147/Ed: W.J. Williams; E. Beutler: A.J. Erslev: M.A. Lichtman, Month not available.

Grutzmacher, P. et al/Effect of Recombinant Human Erythropoietin on Iron Balance in Maintenance Hemodialysis: Theoretical Considerations, Clinical Experience and Consequences/Clinical Nephrology/(1992) 38 Suppl 1: S92–S97, Month not available.

Shuman, M./Hemorrhagic Disorders: Abnormalities of Platelet and Vascular Function–Mechanisms of Hemostasis/Cecil Textbook of Medicine/(1992) 987–999/Ed:J.B.Wyngaarden; L.H. Smith:J.C. Bennett/W.B. Saunders Co/Philadelphia, Month not available.

Schulz, G.E. & Schirmer, R.H./Principles of Protein Stucture/Springer–Verlag/(1979) Table 1–2.

Marotta, C.A. et al/Human β–Globin Messenger RNA–III. Nucleotide Sequences Derived from Complementary DNA/JBC/(1977) 252: 5040–5053, Month not available.

Zoller, M.J. & Smith, M./Oligonucleotide–Directed Mutagenesis of DNA Fragments Cloned Into M13 Vectors/Methods in Enzymology/(1983) 100:468–500/Academic Press, Inc., Month not available.

Mertelsmann, R.H. et al/In Vivo Biology and Therapeutic Potential of Hematopoietic Growth Factors and Peripheral Blood Progenitor Cells/Application of Basic Science to Hematopoiesis and the Treatment of Disease/(1993) Ed: ED. Thomas; S.K. Carter/Raven Press. NY/177–202, Month not available.

Nicola, N.A./Hematopoietic Growth Factors and Their Receptors–An Overview/Application of Basic Science to Hematopoiesis and the Treatment of Disease/Ed: E.D. Thomas. S.K. Carter/Raven Press. NY/(1993) 51–69, Month not available.

McCracken, A.A. et al/An Enrichment Selection for Mutants Resulting from Oligonucleotide–Directed Mutagenesis of Double–Stranded DNA/Biotechniques/(1988) 6(4): 332–339, Month not available.

Luisi, B.F. & Nagai, K/Crystallographic Analysis of Mutant Human Haemoglobins Made in *Escherichia Coli*/Nature/(1986) 320 555–556, Month not available.

Creighton, T.E./Proteins Structures and Molecular Principles/(1993) Fig. 3–9, Month not available.

Dickerson, R.E. & Geis. L./Hemoglobin: Structure, Function, Evolution, and Pathology/(1983) Chapter 3/Benjamin/Cummings Publishing Company, Inc., Month not available.

Liebhaber, S.A. et al/Cloning and Complete Nucleotide Sequence of Human 5'–α–Globin Globin Gene/PNAS USA/(1980) 77(12): 7054–7058, Month not available.

Huang, C.M. et al/Nutritional Status of Patients with Acquired Immunodeficiency Syndrome/Clin. Chem./(1988) 34(10): 1957–1959, Month not available.

Rabiner, S.F. et al/Evaluation of a Stroma–Free Hemoglobin Solution for Use as a Plasma Expander/J. Exp., Med./(1967) 126: 1127–1142, Month not available.

Sunder–Plassmann, L. et al/Stromafree Haemoglobin Solution as a Blood Replacement Fluid Actual State and Problems/Europ. J. Intensive Care Med./(1975) 1: 37–42, Month not available.

Devenuto, F. et al./Appraisal of Hemoglobin Solution as a Blood Substitute/Surgery, Gynecology & Obstetrics/(1979) 149: 417–436, Month not available.

Amberson, W.R. et al./Clinical Experience with Hemoglobin–Saline Solutions/J. of Applied Phys.(1949) 1(7): 469–489, Month not available.

Kaplan, M.E./Acquired Hemolytic Disorders/Cecil Textbook of Medicine/Ed: J.B. Wyngaarden: Smith, L.H.; Bennett, J.C./W.B. Saunders Co Publishing/Philadelphia/(1992) 865–872, Month not available.

Naswitis, K./Ueber Auslosung Von Zell Vermehrungen Durch Wundhormone Bei Hoheren Saugetieren Und Dem Menschen/Dtsch. Med. Wochenschrift/(1922) 48: 187–188, Month not available.

Hooper, C.W. et al./Blood Regeneration Following Simple Anemia–V. The Influence of Blaud's Pills and Hemoglobin/Am J. of Phys./(1920) 53(2) 263–282, Month not available.

Nathan, D.G./Hematologic Diseases–Introduction to Hematologic Diseases/Cecil Textbook of Medicine/ED.J.B. Wyngaarden: L.H. Smith; J.C. Bennett/W.B. Saunders Co/Philadelphia/(1992) 817–836, Month not available.

Bagby, G.C./Leukopenia/Cecil Textbook of Medicine/J.B. Wyngaarden: L.H. Smith: J.C. Bennett/W.B. Saunders Co/Philadelphia/(1992) 907–914, Month not available.

Erslev, A.J./Erythrokinetics–Production of Erythrocytes/Hematology/Ed. W.J. Williams; McGraw–Hill, Inc. Publishing/New York/(1990) 389–407, Month not available.

Bagby, G.C./Leukocytosis and Leukemoid Reactions/Cecil Textbook of Medicine/Ed:J.B. Wyngaarden: L.H. Smith:J.C. Bennett/W.B. Saunders Co/Philadelphia/(1992) 914–920, Month not available.

Nagai, K. et al/Distal Residues in the Oxygen Binding Site of Haemoglobin Studied by Protein Engineering/Nature/(1987) 329: 858–860, Month not available.

Lindenbaum, J./An Approach to the Anemias/Cecil Textbook of Medicine/Ed: J.B. Wyngaarden: L.H. Smith;J.C. Bennett/W.B. Saunders Co/Philadelphia/(1992) 822–831, Month not available.

Winslow, W.M./Hemoglobin–Based Red Cell Substitutes/The Johns Hopkins Univ. Press/Baltimore/(1992) Entire Text, Month not available.

Adachi et al/Comparison of Mechanism of Hemoglobin Denaturation by Heat and Mechanical Shaking/Fed. Proc./(1976) V35, N7, 1392, Month not available.

Adachi & Asakura/Aggregation and Crystallization of Hemoglobins A, S, and C/The J. of Biological Chem./(1981) 256(4): 1824–1830, Month not available.

Adachi & Asakura/Effect of 2,3–Diphosphoglycerate and Inositol Hexaphosphate on the Stability of Normal and Sickle Hemoglobins/Biochemistry/(1974) 13(24): 4976–4982, Month not available.

Cleland et al/The Development of Stable Protein Formulations: A Close Look at Protein Aggregation, Deamidation, and Oxidation/Crit. Reviews in Therapeutic Drug Carrier Systems/(1993) 10(4): 307–377, Month not available.

Feola et al/Mechanisms of Toxicity of Hemoglobin Solutions/Biomat., Art. Cell, Art. Org., (1988) 16(1–3): 217–226, Month not available.

Moore et al/Evaluation of Methemoglobin Formation During the Storage of Various Hemoglobin Solutions/Artif. Organs./(1992) 16(5): 513–518, Month not available.

Pristoupil & Marik/On the Hydrodynamic Instability of Hemoglobin Solutions/Biomat., Art.Cells, Art. Org./(1990) 18(2) 183–188, Month not available.

* cited by examiner

STABILIZED COMPOSITIONS CONTAINING HEMOGLOBIN

CROSS-REFERENCES TO RELATED APPLICATIONS

This application is a continuation-in-part of application Ser. No. 08/399,899, filed Mar. 7, 1995, now abandoned, which is a continuation-in-part of co-pending application Ser. No. 08/208,740 filed Mar. 8, 1994, both incorporated herein by reference in their entirety.

FIELD OF INVENTION

The present invention relates to novel hemoglobin-containing compositions stabilized to inhibit aggregate formation therein.

BACKGROUND OF THE INVENTION

The oxygen carrying portion of red blood cells is the protein hemoglobin. Hemoglobin is a tetrameric protein molecule composed of two identical alpha globin subunits ($\alpha_1$, $\alpha_2$), two identical beta globin subunits ($\beta_1$, $\beta_2$) and four heme molecules. A heme molecule is incorporated into each of the alpha and beta globins to give alpha and beta subunits. Heme is a large macrocyclic organic molecule containing an iron atom; each heme can combine reversibly with one ligand molecule such as oxygen. In a hemoglobin tetramer, each alpha subunit is associated with a beta subunit to form two stable alpha/beta dimers, which in turn associate to form the tetramer. The subunits are noncovalently associated through Van der Waals forces, hydrogen bonds and salt bridges.

Hemoglobin in solution can be used, for example, as a blood substitute, as a therapeutic for enhancing hematopoiesis, as a means of delivering oxygen or enhancing oxygen delivery to tissues, for hemoaugmentation, for the binding or delivery of nitric oxide or other non-oxygen ligands, as a drug delivery vehicle, as a cell culture additive, as a reference standard, and as an imaging agent. However, storage of hemoglobin solutions can be problematic Proteins in solution can form aggregates upon long term storage, changes in temperature during storage, or mechanical agitation (Cleland, et al., *Crit. Rev. Ther. Drug Carrier Systems* 10: 307–377 (1993). To address these problems, many unique formulations have been developed for the stabilization of different proteins in solution. For example, both naturally derived and recombinantly produced proteins have been formulated in solutions containing disaccharides and amino acids (factor VII or factor IX solutions described in PCT Publication WO 91/10439 (1991) to Octapharma), human serum albumin (interleukin-2 solutions described in U.S. Pat. No. 4,645,830 to Yasushi et al.), and glycine, mannitol and non-ionic surfactants (human growth hormone solutions described in U.S. Pat. No. 5,096,885 to Pearlman et al.). Although some general guidance is available for the determination of suitable components for formulations for protein solutions, because of the unique nature of individual proteins, no single formulation is suitable for all different proteins. Indeed, Cleland et al. (1993) state that the creation of a formulation that minimizes protein degradation is difficult because there are many factors that interact to determine protein degradation in a formulation. They go on to state that "protein degradation . . . cannot be predicted a priori and must be determined for each protein".

To extend the storage stability of hemoglobin solutions by limiting autooxidation, hemoglobin has been formulated with reducing agents such as cysteine or dithionite, mannitol, glucose and/or alpha tocopherol (Shorr et al., PCT Publication WO 94/01452 (1994)), in saline solutions or lactated Ringer's solutions that have been modified by the addition of, for example ascorbate, ATP, glutathione and adenosine (Feola et al., PCT Publication WO 91/09615 (1991); Nelson et al, PCT Publication WO 92/03153), under deoxygenated conditions with no exogenous reductants (Kandler and Spicussa, PCT Publication WO 92/02239 (1992)), or in the presence of reducing enzyme systems (Sehgal et al., U.S. Pat. No. 5,194,590). These hemoglobin formulations have been designed to minimize autooxidation of the protein molecule, but none have been designed that specifically reduce the aggregation of the hemoglobin molecules during storage.

Nonetheless, the aggregation of hemoglobin molecules during storage poses significant problems. Moore et al., *Art. Org.* 16: 513–518 (1992) caution that hemoglobin should not be stored in the frozen state due to the formation of aggregates or precipitates. Moreover, the formation of aggregates in hemoglobin solutions agitated at room temperature has been observed in numerous formulations (Pristoupil and Marik, *Biomat. Art. Cells, Art. Org.*, 18: 183–188, 1990; Adachi and Asakura, *J. Biol. Chem.*, 256: 1824–1830, 1981; Adachi and Asakura, *Biochem.*, 13: 4976–4982, 1974). This aggregation of the hemoglobin protein molecule typically does not occur as a result of autooxidation of the hemoglobin heme iron, but rather by interaction of the hemoglobin molecules (Adachi et al., *Fed. Proc.* 35: 1392 (1976). Aggregates in hemoglobin solutions can increase immunogenicity, reduce functionality and reduce the activity of the protein solution (Cleland et al., supra; Feola et al., *Biomat. Art. Cells Art. Org.* 16: 217–226 (1988).

Accordingly, there is a need for hemoglobin compositions stabilized against the formation of aggregates. The present invention satisfies this need and provides related advantages as well.

SUMMARY OF THE INVENTION

The present invention relates to compositions containing hemoglobin wherein the hemoglobin is stabilized with a surfactant to inhibit the formation of aggregates. In one embodiment, compositions of the invention contain about 0.001% to about 90% by weight to volume hemoglobin and 0.01 to 1% (weight to volume) of a surfactant and can also include 0–200 mM of one or more buffers, 0–200 mM of one or more alcohols or polyalcohols, 0–300 mM of one or more salts and 0–5 mM of one or more reducing agents. In a further embodiment, the compositions can contain 0.1–50% by weight to volume of hemoglobin, 0–50 mM of one or more buffers, 0–200 mM of one or more salts, 0.02%–0.5% (weight to volume) of one or more surfactants, 0–5 mM of one or more reducing agents and is at pH of about 6.8 to 7.8. Another aspect of the invention are compositions containing about 1 to about 20% by weight to volume of hemoglobin, 5–15 mM sodium phosphate, 100–185 mM sodium chloride, 0.02%–0.08% (weight to volume) polysorbate 80, 1–4 mM of ascorbate and is at pH of about 6.8 to 7.6. A still further embodiment of the present invention is a method for stabilizing compositions containing hemoglobin to inhibit the formation of aggregates comprising adding to the composition a stabilizing amount of a surfactant.

Other features and advantages of the invention will be apparent from the following description of the invention and from the claims.

DETAILED DESCRIPTION OF THE INVENTION

Figure 1:
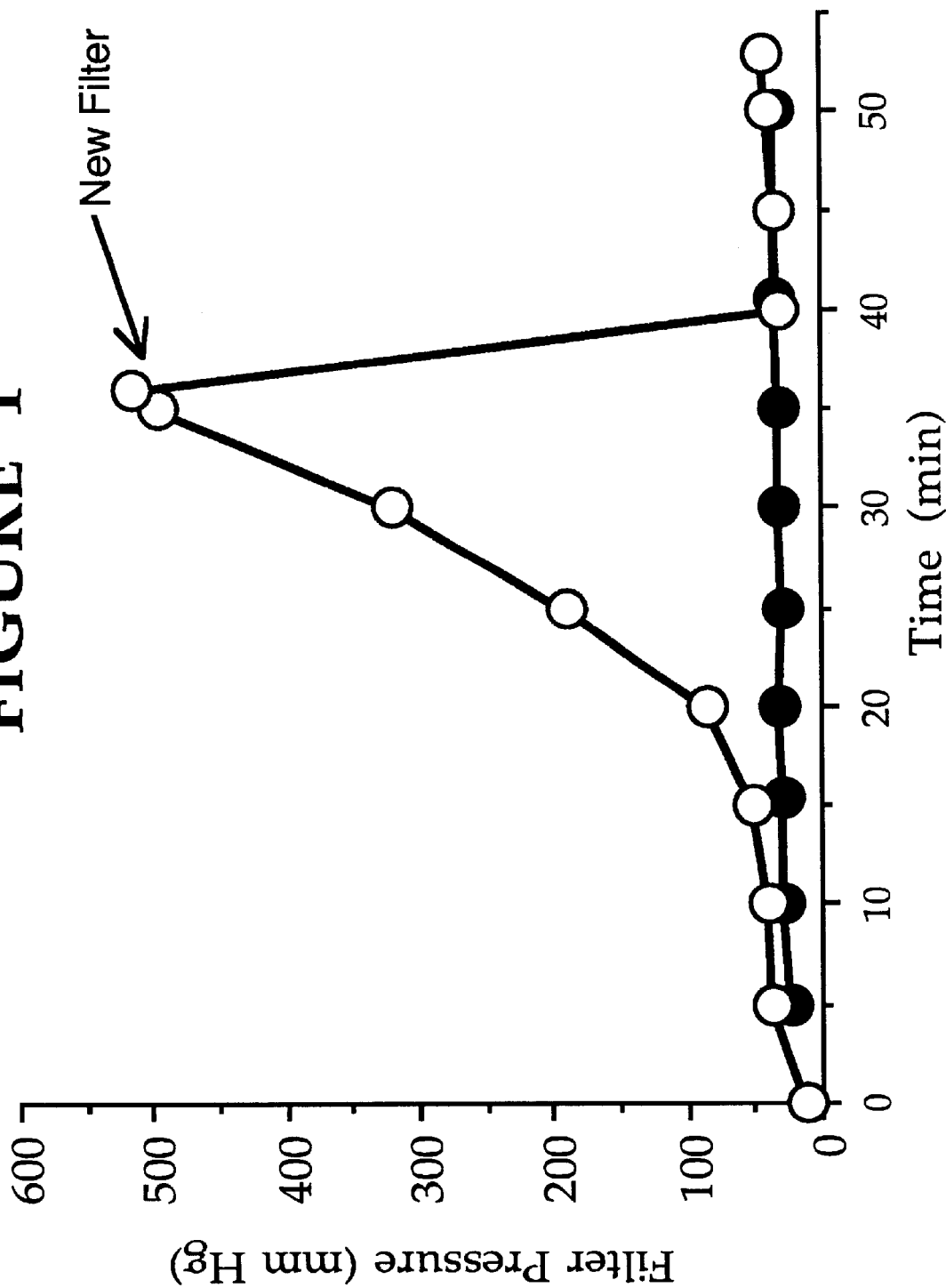
FIG. 1 shows filter pressure during filtration of hemoglobin formulated in a mannitol/bicarbonate buffer system. Open circles show the filter pressure for the mannitol/bicarbonate formulation that did not contain polysorbate 80. Filled circles show the filter pressure for the mannitol/bicarbonate formulation that contained 0.03% polysorbate 80.

Hemoglobin is generally a tetramer composed of two alpha globin subunits ($\alpha 1$, $\alpha 2$) and two beta globin subunits ($\beta_1$, $\beta_2$). There is no sequence difference between $\alpha_1$ and $\alpha_2$ or between $\beta_1$ and $\beta_2$. The subunits are noncovalently associated by Van der Waals forces, hydrogen bonds and salt bridges.

Hemoglobin is readily available from a number of natural and recombinant sources. For example, slaughter houses produce very large quantities of hemoglobin-containing blood. Particular species or breeds of animals which produce a hemoglobin especially suitable for a particular use can be specifically bred in order to supply hemoglobin. Transgenic animals can be produced that can express non-endogenous hemoglobin (Logan, J. S. et al., PCT Application Number PCT/US92/05000). Human hemoglobin can be collected from outdated human blood that must be discarded after a certain expiration date.

In addition to extraction from animal sources, the genes encoding subunits of a desired naturally occurring or mutant hemoglobin can be cloned, placed in a suitable expression vector and inserted into an organism, such as a microorganism, animal or plant, or into cultured animal or plant cells or tissues. These organisms can be produced using standard recombinant DNA techniques and hemoglobin produced by these organisms can then be expressed and collected (as described, for example, in Hoffman, S. J and Nagai, K. in U.S. Pat. No. 5,028,588 and Hoffman, et al., WO 90/13645 (1990), both herein incorporated by reference).

Purification of hemoglobin from any source can be accomplished using purification techniques which are known in the art. For example, hemoglobin can be isolated and purified from outdated human red blood cells by hemolysis of erythrocytes followed by chromatography (Bonhard, K, et al., U.S. Pat. No. 4,439,357; Tayot, J. L. et al., EP Publication 0 132 178 (1985); Hsia, J. C., EP Patent 0 231 236 B1 (1991)), filtration (Rabiner, S. F. (1967) et al., *J. Exp. Med.* 126: 1127–1142; Kothe, N. and Eichentopf, B. U.S. Pat. No. 4,562,715), heating (Estep, T. N., PCT publication PCT/US89/014890, Estep, T. N., U.S. Pat. No. 4,861,867), precipitation (Simmonds, R. S and Owen, W. P., U.S. Pat. No. 4,401,652; Tye, R. W., U.S. Pat. No. 4,473,494) or combinations of these techniques (Rausch, C. W. and Feola, M., EP 0 277 289 B1 (1088)). Recombinant hemoglobins produced in transgenic animals have been purified by chromatofocusing (Townes, T. M. and McCune, PCT publication PCT/US/09624); those produced in yeast and bacteria have been purified by ion exchange chromatography (Hoffman, S. J and Nagai, K in U.S. Pat. No. 5,028,588 and Hoffman, et al., WO 90/13645 (1990)).

As used herein, "hemoglobin" means a hemoglobin molecule comprised of at least two globin subunits or domains (dimeric). Hemoglobin can be free in solution or contained within in a cell, liposome or the like. Any globin subunit, whether of natural or recombinant origin, of any hemoglobin, can be crosslinked or genetically fused to another globin subunit. Such crosslinking or genetic fusion can occur within a single hemoglobin molecule or between two or more hemoglobin molecules. Particularly preferred hemoglobins are tetrameric hemoglobins, whether or not genetically fused or chemically crosslinked, and multiples of tetrameric hemoglobins (e.g. octamers, dodecamers, etc.), however produced. Therefore, the term hemoglobin encompasses any for example, non-crosslinked hemoglobin, chemically crosslinked hemoglobin, or genetically fused hemoglobin. In addition, the hemoglobin can be either liganded with any ligand, such as oxygen, carbon monoxide or nitric oxide, or can be in the unliganded (deoxygenated) state.

"Surfactant" as used herein is intended to encompass any detergent that has a hydrophilic region and a hydrophobic region, and, for the purposes of this invention includes non-ionic, cationic, anionic and zwitterionic detergents. Suitable surfactants include, for example, N-laurylsarcosine, cetylpyridinium bromide, polyoxyethylene sorbitan monolaurate (also known as polysorbate 20 or "TWEEN" 20), polyoxyethylene glycol hexadecyl ether ("BRIJ" 35), or polyoxyethylene sorbitan monooleate (also known as polysorbate 80 or "TWEED" 80). A non-ionic surfactant is preferable for the formulations described herein. Such non-ionic surfactants can be chosen from block co-polymers such as a polyoxamer or polyoxyethylene sorbitan fatty acid esters, for example, polysorbate 20 or polysorbate 80. Polysorbate 80 is preferred for the compositions of this invention.

A stabilizing amount of surfactant is an amount sufficient to inhibit the formation of aggregates in hemoglobin-containing compositions. Such aggregate formation can occur during, for example, long term storage, freezing and thawing, or mechanical agitation. Inhibition of such aggregate formation occurs when the aggregate formation in a composition containing hemoglobin and a surfactant is significantly inhibited relative to aggregate formation in the same composition containing hemoglobin that does not contain the surfactant. Significant inhibition of aggregation occurs when aggregate formation is at least 10% less in the hemoglobin containing composition with surfactant than in a comparable formulation that does not contain surfactant, preferably at least 50% less, more preferably at least 70% less, and most preferably at least 90% less. "Aggregates" refers to hemoglobin molecules that can be soluble or insoluble and are detectable by aggregate detection methods such as visual inspection, light scattering methods such as spectrophotometry and dynamic light scattering, particle counting methods, filtration backpressure increases or other suitable methods for the determination of aggregates.

The compositions of the invention can be incorporated in conventional formulations including but not limited to tablets, capsules, caplets, compositions for subcutaneous, intravenous, or intramuscular injection or oral administration, reagent solutions for standardization of clinical instrumentation, large volume parenteral solutions useful as blood substitutes, etc. The compositions can be formulated by any method known in the art, including, for example, simple mixing, sequential addition, emulsification, and the like. The formulations of the invention comprise hemoglobin and surfactants as the active ingredients and can include other active or inert agents. For example, a parenteral therapeutic composition can comprise a sterile isotonic saline solution containing between 0.001% and 90% (w/v) hemoglobin. Suitable compositions can also include 0–200 M of one or more buffers (for example, acetate, phosphate, citrate, bicarbonate, or Good's buffers). Salts such as sodium chloride, potassium chloride, sodium acetate, calcium chloride, magnesium chloride can also be included in the compositions of the invention at concentrations of 0–2 M. In addition, the compositions of the invention can include 0–2 M of one or more carbohydrates (for example, reducing carbohydrates such as glucose, maltose, lactose or non-reducing carbohydrates such as sucrose, trehalose, raffinose, mannitol, isosucrose or stachyose) and 0–2 M of one or more alcohols or poly alcohols (such as polyethylene glycols, propylene glycols, dextrans, or polyols). The compositions of the invention also contain 0.005–1% of one or more surfactants. The compositions of the invention can also be at about pH 6.5–9.5. In another embodiment, the composition contains 0–300 mM of one or more salts, for example chloride salts, 0–100 mM of one or more non-reducing sugars, 0–100 mM of one or more buffers, and 0.01–0.5% of one or more surfactants. In a still further embodiment, the composition contains 0–150 mM NaCl, 0–10 mM sodium phosphate, and 0.01–0.1% surfactant, pH 6.6–7.8. Most preferably, the hemoglobin-containing composition includes 5 mM sodium phosphate, 150 MM NaCl, and 0.025% to 0.08% polysorbate 80, pH 6.8–7.6.

Other components can be added if desired. For example 0–5 mM reducing agents such as dithionite, ferrous salts, sodium borohydride, and ascorbate can be added to the composition, most preferably 0.5–3 mM ascorbate is added to the composition. Additional additives to the formulation can include anti-oxidants (e.g. ascorbate or salts thereof, alpha tocopherol), anti-bacterial agents, oncotic pressure agents (e.g. albumin or polyethylene glycols) and other formulation acceptable salts, sugars and excipients known to those of skill in the art.

Each formulation according to the present invention can additionally comprise inert constituents including carriers, diluents, fillers, salts, and other materials well-known in the art, the selection of which depends upon the particular purpose to be achieved and the properties of such additives which can be readily determined by one skilled in the art.

The formulations of the instant invention can be used in compositions useful as substitutes for red blood cell transfusions in any application that such transfusions are used. Such applications and methods of using the formulations blood substitution applications can be readily determined by one skilled in the art. For example, such compositions of the instant invention formulated as blood substitutes can be used for the treatment of hemorrhage, anemia, and acute normovolemic hemodilution. Moreover, the formulations of the instant invention are also useful in compositions suitable, for example, for the enhancement of hematopoiesis, for the binding or delivery of nitric oxide or non-oxygen ligands in vivo or in vitro, for the enhancement of cell growth in cell culture, as drug delivery vehicles, as reference standards for analytical assays and instrumentation, and as imaging agents.

EXAMPLES

The following examples are provided by way of describing specific embodiments of the present invention without intending to limit the scope of the invention in any way.

Example 1

Measurements of Aggregate Formation

Measurement of particles $\geq 2$ $\mu$m

Light obscuration functions by measuring the decrease in signal strength caused by a particle passing through a laser. By comparing the decrease in signal strength to that of a series of latex spheres of known size, the sizes of the particles in the sample were determined. Particles $\geq 2$ $\mu$m were measured by light obscuration with a HIAC/Royco (Silver Springs, Md.) particle counter model 8000A equipped with a model 3000 sampler. Measurements were made following dilution of the sample (0.5–1 ml aliquots) to 10 ml in 150 mM NaCl, 5 mM sodium phosphate buffer, pH 7.4. Numbers represent the cumulative particle counts $\geq 2$ $\mu$m.

Filter pressure assay

As a solution is passed through a filter, the filter is slowly blocked and the filter pressure increases as a function of aggregate accumulation on the filter. This method provides an indirect measurement of aggregation $\geq 0.2$ $\mu$m which is not detectable by the light obscuration described above. The ability of a hemoglobin-containing sample to block a 0.2 $\mu$m filter was determined using an "IVAC" infusion pump (San Diego, Calif.). Briefly, following shaking or freeze/thawing each sample was transferred to a 500 ml polyvinyl chloride bag and pumped at 500 ml/hr through a 0.2 $\mu$m "PALL" in-line filter (East Hills, N.Y.). The back pressure on the filter was monitored directly from the "IVAC" pump.

Example 2

Determination of Concentration of Polysorbate 80 required to inhibit formation of aggregates $\geq 2$ $\mu$m during freeze/thaw Hemoglobin was expressed, prepared and purified as described in co-owned PCT patent application number, PCT/US94/13034, filed Nov. 14, 1994, entitled "Purification of Hemoglobin" and incorporated herein by reference. Suitable concentrations of polysorbate 80 for reduction of aggregation were determined by subjecting hemoglobin formulated with increasing concentrations of polysorbate 80 to repeated freeze/thaw cycles. Aliquots (1.5 ml) of 50 mg/ml hemoglobin in 150 mM NaCl, 5 mM phosphate, pH 7.4, were formulated with and without polysorbate 80 and sealed in 3.5 ml glass vials. The samples were frozen at either $-80°$ C. or $-20°$ C. for 24 hour periods. On selected days two vials were removed from each freezer, slowly thawed in water at $25°$ C. and the number of aggregates determined using the HIAC/Royco Particle Counter. The remaining samples were thawed at room temperature then refrozen at either $-80°$ C. or $-20°$ C.

In the absence of polysorbate 80 the number of aggregates $\geq 2$ $\mu$m increased by approximately 3-fold at $-20°$ C. (Table 1) and approximately 5-fold at $-80°$ C. (Table 2) after five freeze/thaw cycles. The presence of 0.005–0.01% polysorbate 80 could not prevent the increase at either temperature and at $-20°$ C. appeared to exacerbate the increase in aggregation seen in the absence of polysorbate. In contrast, 0.025–0.1% polysorbate 80 inhibited the formation of aggregates after the freeze/thaw cycles relative to the formation of aggregates in compositions that did not contain polysorbate by between approximately 28–46%. During the course of the freeze/thaws the number of aggregates in the samples containing 0.025% polysorbate 80 varied from 1–1.6-fold at $-20°$ C. and from 1.2–1.9-fold at $-80°$ C. Furthermore, the final degree of aggregation in formulations containing 0.05 to 0.1% polysorbate 80 was significantly less (~45–70%) than the aggregation observed in compositions that did not contain surfactant. The samples containing 0.025% polysorbate 80 or greater demonstrated a decreased tendency to aggregate compared to the samples containing 0.01% or less (inhibition of aggregate formation in the presence of 0.025% polysorbate was at least 25% relative to formulations that did not contain surfactant).

TABLE 1

Effect of Polysorbate 80 on particle aggregation: Freeze/Thaw −20 °C.
Number Freeze/Thaw Cycles

| % (w/v) Polysorbate 80 | 0 | 2 | 5 |
|---|---|---|---|
| 0.0% | 1500 | 3300 | 4200 |
| 0.005% | 3800 | 5100 | 7200 |
| 0.01% | 3000 | 4200 | 7500 |
| 0.025% | 2000 | 3200 | 3000 |
| 0.05% | 1400 | 1900 | 2300 |
| 0.1% | 970 | 1800 | 2200 |

TABLE 2

Effect of Polysorbate 80 on particle aggregation: Freeze/Thaw −80 °C.
Number Freeze/Thaw Cycles

| % (w/v) Polysorbate 80 | 0 | 2 | 5 |
|---|---|---|---|
| 0.0% | 1500 | 3300 | 7800 |
| 0.005% | 3800 | 5500 | 9000 |
| 0.01% | 3000 | 4300 | 5600 |
| 0.025% | 1955 | 3100 | 3600 |
| 0.05% | 1400 | 2700 | 2300 |
| 0.1% | 1000 | 2000 | 2400 |

Example 3

Determination of Concentration of Polysorbate 80 required to inhibit formation of aggregates ≧2 µm during mechanical agitation Hemoglobin was prepared as described in Example 2. Suitable concentrations of polysorbate 80 for reduction of aggregation were determined by subjecting hemoglobin formulated with increasing concentrations of polysorbate 80 to mechanical agitation. Aliquots (1.5 ml) of 50 mg/ml hemoglobin in 150 mM NaCl, 5 mM phosphate, pH 7.4, were formulated with and without polysorbate 80 and were sealed in 3.5 ml glass vials. The samples were then placed on their sides on an orbital shaker and shaken for 1 hour at 4° C. at 90, 120, 180 and 240 rpm. A 1 ml aliquot was removed and aggregates ≧2 µm were counted using a HIAC/Royco Particle counter as described in Example 1. Because no aggregate formation occurred during the course of the experiment at 90 or 120 rpm, only the control data (no mechanical agitation, listed as 0 rpm in Table 3) and the data for 180 and 240 rpm are reported below (Table 3). Addition of the surfactant at a concentration of 0.025% or greater inhibited the formation of aggregates while addition of 0.01% of the surfactant did not demonstrate any significant protection against aggregation. At 240 rpm the sample containing 0.025% polysorbate 80 showed an increase in the number of aggregates compared to the 0.05% polysorbate 80 sample. In other experiments no increase in aggregation was observed by decreasing the polysorbate concentration from 0.05% to 0.025%.

TABLE 3

Effect of Polysorbate 80 on particle aggregation: Mechanical Agitation

| % (w/v) Polysorbate 80 | 0 rpm | 180 rpm | 240 rpm |
|---|---|---|---|
| 0.0% | 2200 | 140,000 | 570,000 |
| 0.0125% | 1800 | 110,000 | 710,000 |
| 0.025% | 2100 | 3700 | 18,000 |
| 0.05% | 1400 | 1100 | 5500 |

Example 4

Determination of concentration of polysorbate 80 required to inhibit increases in filtration backpressure: mechanical agitation Hemoglobin was prepared as described in Example 2 and formulated in either 150 mM NaCl, 5 mM sodium phosphate, pH 7.4 (NaCl/sodium phosphate formulation) or 100 mM NaCl, 50 mM mannitol, 3 mM KCl, 2 mM $CaCl_2$, 1 mM $MgCl_2$ and 10 mM $NaHCO_3$, pH 7.6 (mannitol/bicarbonate formulation). Controls did not have polysorbate 80 added to the formulations while the test solutions of both the NaCl/sodium phosphate formulation and the mannitol/bicarbonate formulation contained 0.03% polysorbate 80. Aliquots (500 ml) of control and test hemoglobin solutions were placed in 1 L polycarbonate bottles and were agitated for 1 hour at 4° C. on an orbital shaker at 180 rpm. Following shaking, an aliquot (1 ml) of each sample was removed for particle content determination using the Hiac/Royco instrumentation as described above. The remaining volume of each sample was then transferred into a polyvinyl chloride bag and pumped through a 0.2 µm PALL in-line filter at 500 ml/hour using an IVAC infusion pump. The filter pressure was monitored directly from the IVAC pump.

The hemoglobin formulated without polysorbate 80 blocked the filter within 3 minutes irrespective of the other components of the solution (i.e. salts, etc.). In contrast, in the presence of polysorbate 80, ~500 ml of material formulated in either formulation did not cause overpressuring of the filter (backpressure greater than 500 mm Hg) during the course of the filtration. Filter blockage in the formulations that did not contain surfactant was most probably due to the approximately 300–400 fold increase in aggregates ≧2 µm that resulted from mechanical agitation. After one hour of shaking, the mannitol/bicarbonate/no surfactant formulation contained >700,000 counts per ml, while the NaCl/sodium phosphate/no surfactant formulation contained >600,000 counts per ml. Counts per ml were determined using the Hiac/Royco Particle Counter described in Example 1.

Example 5

Determination of concentration of polysorbate 80 required to inhibit increases in filtration backpressure: freeze/thaw Hemoglobin was prepared as described in Example 2 and formulated in either 150 mM NaCl, 5 mM sodium phosphate, pH 7.4 (NaCl/sodium phosphate formulation) or 100 mM NaCl, 50 mM mannitol, 3 mM KCl, 2 mM $CaCl_2$, 1 mM $MgCl_2$ and 10 mM $NaHCO_3$, pH 7.6 (mannitol/bicarbonate formulation). Controls did not have polysorbate 80 added to the formulations while the test solutions of both the NaCl/sodium phosphate formulation and the mannitol/bicarbonate formulation contained 0.03% polysorbate 80.

Aliquots (500 ml) of control and test hemoglobin solutions were placed in 1 L polycarbonate bottles and frozen at −20° C. for 24 hours, then thawed in a 25° C. water bath. The freezing and thawing cycles were repeated three times. After the freezing and thawing, each sample was transferred into a polyvinyl chloride bag and pumped through a 0.2 μm PALL in-line filter at 500 ml/hour using an IVAC infusion pump. The filter pressure was monitored directly from the IVAC pump.

Figure 2:
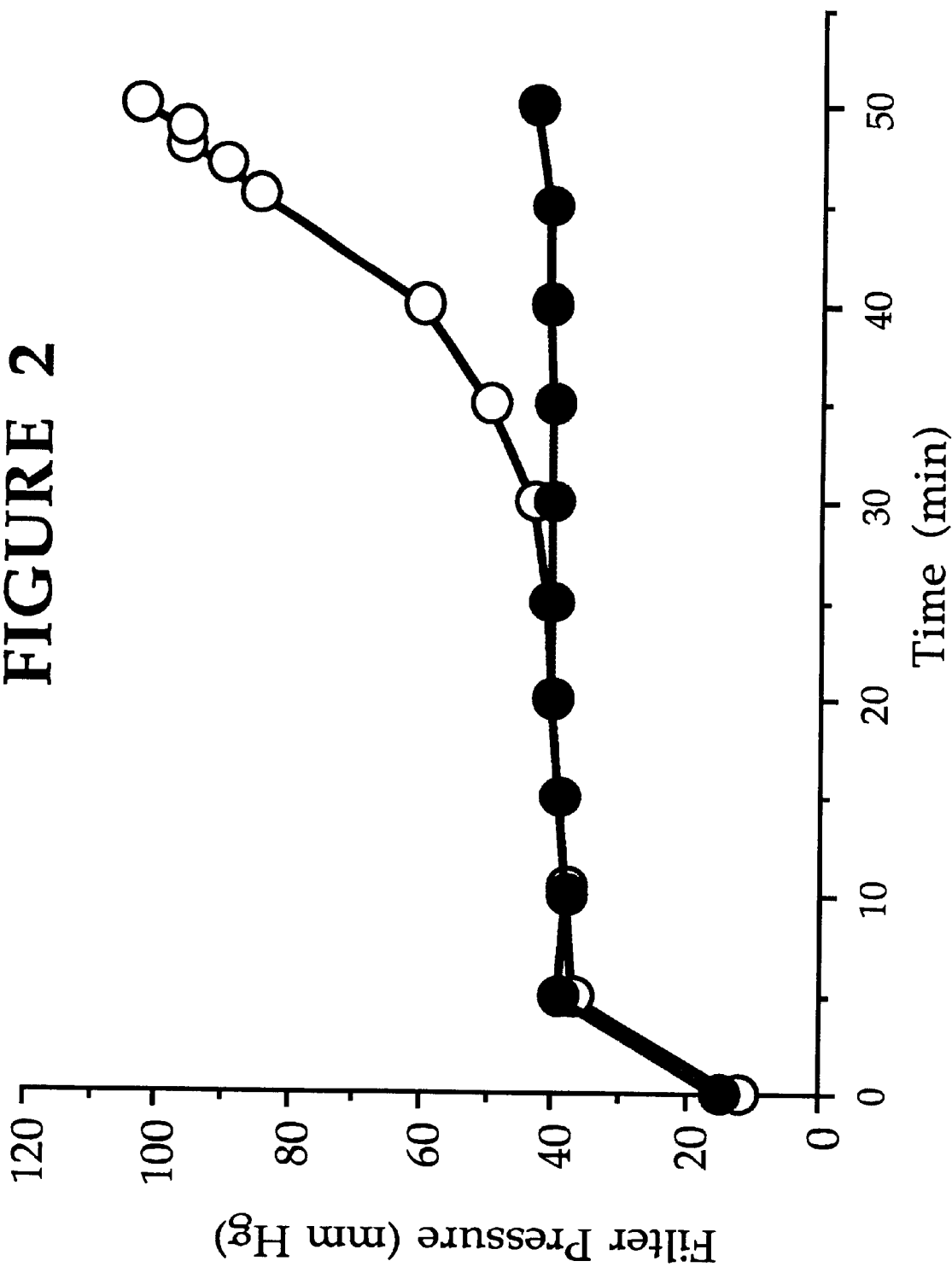
FIG. 2 shows filter pressure during filtration of hemoglobin formulated in a sodium chloride/sodium phosphate buffer system. Open circles show the filter pressure for the sodium chloride/sodium phosphate formulation that did not contain polysorbate 80. Filled circles show the filter pressure for the sodium chloride/sodium phosphate formulation that contained 0.03% polysorbate 80.

Filtration of the material containing polysorbate 80 demonstrated no increase in filter pressure for both formulations (FIGS. 1 and 2). In contrast, the sample in the mannitol/bicarbonate formulation that did not contain polysorbate 80 achieved maximum filter pressure within 35 minutes. After replacement of the filter, backpressure again began to rise following another 12 minutes of filtration (FIG. 1). The NaCl/sodium phosphate/no polysorbate formulation exhibited behavior similar to the mannitol/bicarbonate formulation that did not contain surfactant. Filtration of the NaCl/sodium phosphate/no polysorbate formulation resulted in increasing filtration backpressure during the 50 minutes of filtration FIG. 2).

The foregoing description of the invention is exemplary for purposes of illustration and explanation. It will be apparent to those skilled in the art that changes and modifications will be possible without departing from the spirit and the scope of the invention. It is intended that the following claims be interpreted to embrace all such changes and modifications.

What is claimed is:

1. A composition comprising purified hemoglobin and a stabilizing amount of surfactant.

2. A composition according to claim 1 wherein the surfactant is a non-ionic surfactant.

3. A composition according to claim 2 wherein the surfactant is selected from the group consisting of polyoxamer fatty acid esters and polyoxyethelene sorbitan fatty acid esters.

4. A composition according to claim 3 wherein the polyoxyethelene sorbitan fatty acid ester is polysorbate 80.

5. A composition according to claim 2 wherein the surfactant is 0.01 to 1% by weight.

6. A composition according to claim 5 wherein the surfactant is 0.02 to 0.5% by weight.

7. A composition according to claim 6 wherein the surfactant is 0.025 to 0.08% by weight.

8. The composition of claim 2, wherein said purified hemoglobin is recombinant hemoglobin.

9. A composition according to claim 5 comprising:
   about 0.001% to about 90% by weight to volume of purified hemoglobin;
   0–200 mM of one or more buffers;
   0–200 mM of one or more alcohols or polyalcohols;
   0–300 mM of one or more salts;
   0.01–1% of one or more surfactants;
   0–5 mM of one or more reducing agents; and
   pH of about 6.5–9.5.

10. A composition according to claim 9 comprising:
    about 0.01% to about 50% by weight to volume of purified hemoglobin;
    0–50 mM of one or more buffers;
    0–200 mM of one or more salts;
    0.02–0.5% of one or more surfactants;
    0–5 mM of one or more reducing agents; and
    pH of about 6.8–7.8.

11. A composition according to claim 10 comprising:
    about 1% to about 20% by weight to volume of purified hemoglobin;
    5–20 mM of sodium phosphate;
    100–175 mM of sodium chloride;
    0.02–0.08% of polysorbate;
    1–4 mM of ascorbate; and
    pH of about 6.8–7.6.

12. A composition according to claim 10 wherein the salts are chloride salts.

13. A composition according to claim 10 wherein the buffers are phosphate buffers.

14. A composition according to claim 10 wherein the surfactant is a polysorbate.

15. A composition according to claim 13 wherein the surfactant is polysorbate 80.

16. A composition according to claim 10 wherein the reducing agent is ascorbate.

17. A method for stabilizing a composition containing purified hemoglobin comprising formulating with the composition a stabilizing amount of surfactant.

18. The method of claim 17, wherein said purified hemoglobin is recombinant hemoglobin.

* * * * *